US00PP33106P3

(12) United States Plant Patent
Clifton

(10) Patent No.: US PP33,106 P3
(45) Date of Patent: May 25, 2021

(54) ***LYSIMACHIA* PLANT NAMED 'HILLYSSUN'**

(50) Latin Name: *Lysimachia christinae*
Varietal Denomination: Hillyssun

(71) Applicant: Hillier Nurseries Ltd., Romsey (GB)

(72) Inventor: Richard Paul Clifton, Romsey (GB)

(73) Assignee: HILLER NURSERIES LTD., Romsey (GB)

( * ) Notice: Subject to any disclaimer, the term of this patent is extended or adjusted under 35 U.S.C. 154(b) by 0 days.

(21) Appl. No.: 16/873,331

(22) Filed: Mar. 19, 2020

(65) Prior Publication Data

US 2020/0315079 P1 Oct. 1, 2020

(30) Foreign Application Priority Data

Mar. 28, 2019 (QZ) ..... PBR 2019/0818

(51) Int. Cl.
*A01H 5/02* (2018.01)
*A01H 6/00* (2018.01)

(52) U.S. Cl.
USPC ..... Plt./453
CPC ..... *A01H 6/00* (2018.05); *A01H 5/02* (2013.01)

(58) Field of Classification Search
USPC ..... Plt./453
CPC ..... A01H 5/02; A01H 5/00; A01H 6/00
See application file for complete search history.

(56) References Cited

PUBLICATIONS

Facebook post from PlantHaven Inc., 2018, retrieved on Aug. 26, 2020, retrieved from the Internet at https://zh-cn.facebook.com/PlantHavenInc/posts/lysimachia-sunburst-is-our-newest-and-fanciest-trailing-foliage-item-for-a-quick/2046460062060449/, 2 pp. (Year: 2018).*

Plant Haven retrieved on Aug. 26, 2020, retrieved from the Internet at https://www.planthaven.com/plant/lysimachia-sunburst/, 2 pp. (Year: 2020).*

Zheng et al. Lysimachia christinae 'Zixin': A New Groundcover Plant, HortScience 44(2):474-475, 2009. (Year: 2009).*

* cited by examiner

*Primary Examiner* — June Hwu
(74) *Attorney, Agent, or Firm* — Weatherly IP Solutions, LLC; Barbara Campbell

(57) ABSTRACT

A new variety of *Lysimachia* named 'Hillyssun' that is distinguishable by its prostrate or trailing plant habit, dark green rounded leaves which exhibit narrow dark-purple veining, and flowers which are mid-yellow in color except for bright orange-red colored eyes or petal bases, is disclosed.

2 Drawing Sheets

Figure 1:
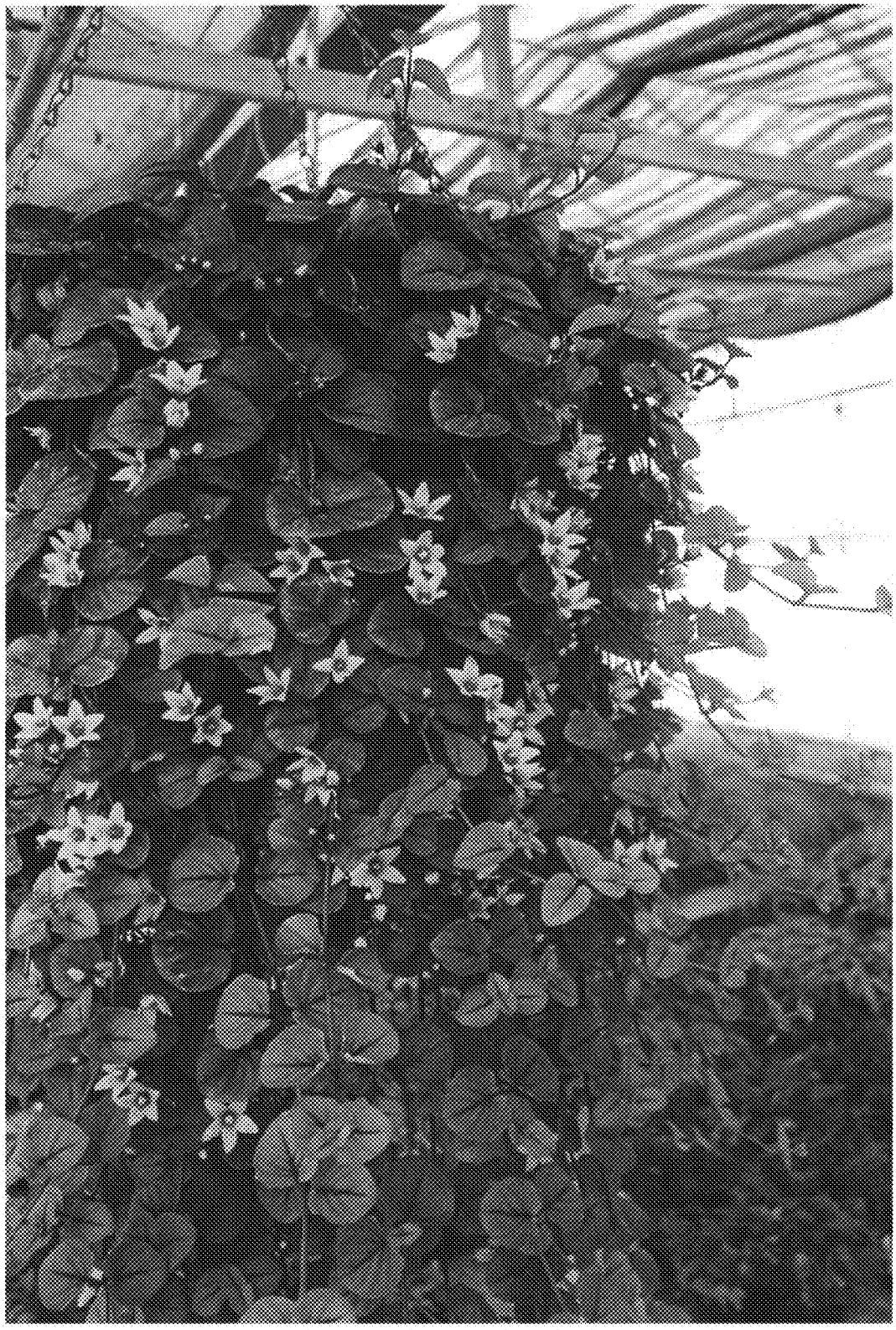

Genus and species: *Lysimachia christinae.*
Variety denomination: 'Hillyssun'.

CROSS-REFERENCE TO RELATED APPLICATIONS

This application claims the benefit of priority under 35 U.S.C. 119(f) to the application for European Community Plant Variety Rights which was filed for the instant plant variety on Mar. 28, 2019, File Number 2019/0818.

BACKGROUND

The present disclosure relates to a new and distinct cultivar of *Lysimachia christinae* whose natural plant habit is prostrate or creeping but which may be grown as an ornamental plant for use in hanging baskets or containers. The new variety will be referred to hereinafter by the variety name 'Hillyssun'.

'Hillyssun' was selected in 2012 by the inventor as a single plant which the inventor had observed at the inventor's nursery in Romsey, Hampshire, United Kingdom within a population of plants which the inventor had raised from seeds saved from open pollinations of the species *Lysimachia christinae*. The inventor observed that this one plant, subsequently named 'Hillyssun' exhibited significant commercial attributes in comparison with plants of the species parent, notably dark-green colored leaves with narrow deep-purple venation, and flowers with deeper yellow petals whose petal bases are bright orange-red giving the appearance of prominent contrasting eyes.

'Hillyssun' was first asexually propagated in 2012 by the inventor at the inventor's nursery in Romsey, Hampshire, United Kingdom using the method of stem cuttings. The inventor has confirmed that 'Hillyssun' is stable and reproduces true to type in successive generations of asexual reproduction.

SUMMARY

The following traits have been repeatedly observed and represent the distinguishing characteristics of 'Hillyssun'. 'Hillyssun' has not been tested under all possible conditions and phenotypic differences may be observed with variations in environmental, climatic, and cultural conditions, without however, any variance in genotype.

1. 'Hillyssun' exhibits a prostrate creeping habit when allowed to remain on the ground.
2. 'Hillyssun' may be grown as a hanging basket or container plant, when the stems hang vertically.

3. The leaves of 'Hillyssun' are rounded, dark-green in color for the upper surface and light-green in color on the lower surface.
4. The veins of the upper surfaces of the leaves of 'Hillyssun' are in part narrow and dark-purple in color.
5. The flowers of 'Hillyssun' are single campanulate and borne in each leaf axil.
6. The flowers of 'Hillyssun" are mid-yellow in color with contrasting orange-red eyes.
7. 'Hillyssun' exhibits summer flowering dormancy in temperatures exceeding 25 degrees Celsius.
8. 'Hillyssun' is attractive when not in flower due to its mid-green leaves with dark-green leaves with dark-purple veining and red-purple stems.
9. After 4 months of growth (started from a rooted cutting) in a one-gallon container, a hanging plant of 'Hillyssun' will exhibit trailing stems approximately 1 meter in length.
10. The stems of 'Hillyssun' are red-purple in color.
11. No seed has been observed in growing plants of 'Hillyssun'.

DESCRIPTION OF THE PHOTOGRAPHS

The accompanying color photograph, FIG. 1, illustrates the overall appearance of the new *Lysimachia* cultivar 'Hillyssun' showing the colors as true as it is reasonably possible to obtain in colored reproductions of this type. The brown discoloration of some upper older leaves has resulted from direct sun stress and is not typical of the variety.

Figure 2:
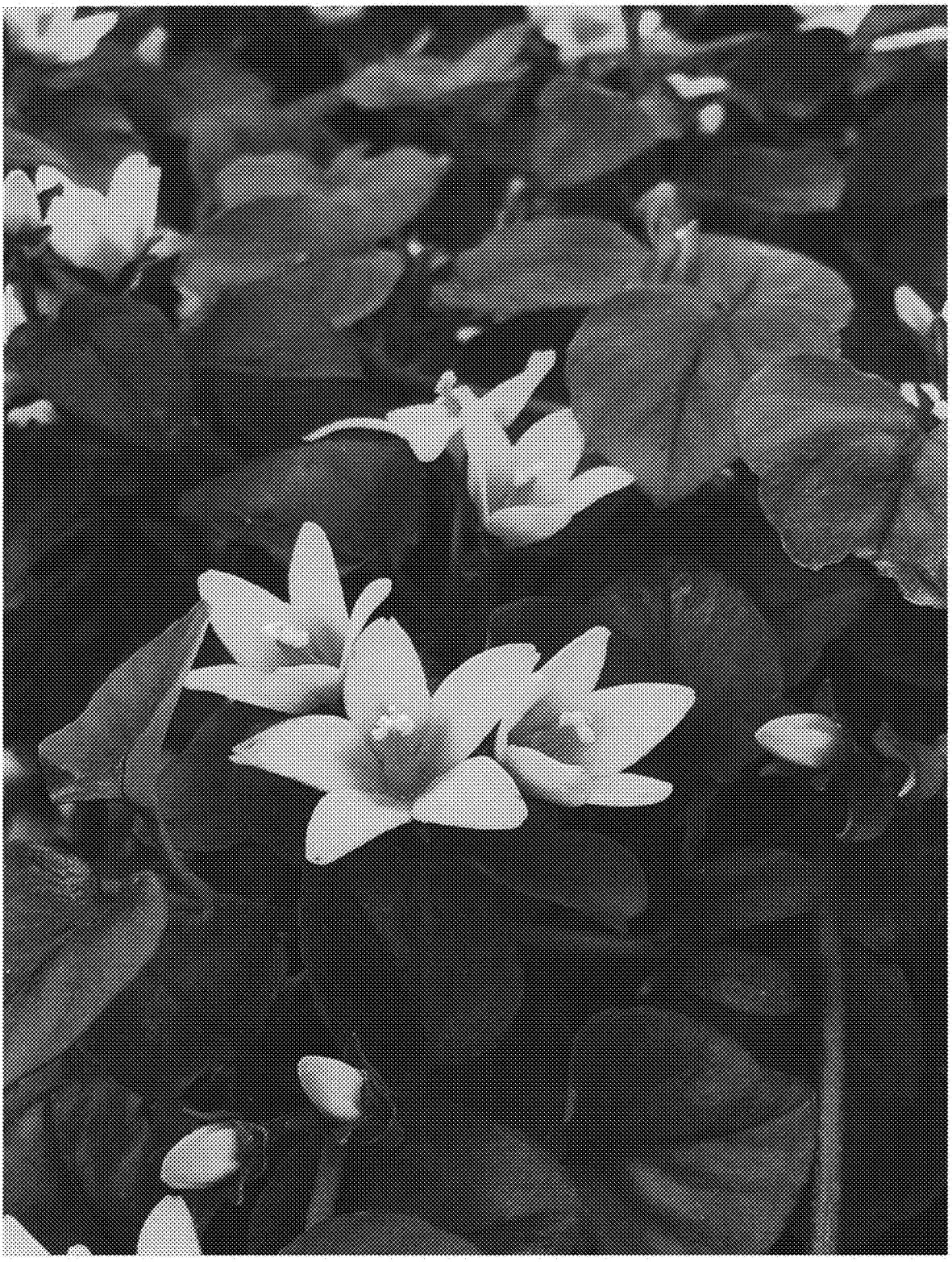

The accompanying color photograph, FIG. 2, illustrates a close-up view of the inflorescences and buds of 'Hillyssun'.

Photographs were taken in October 2018 at the inventor's nursery in Romsey, Hampshire, United Kingdom using an approximately 6-month-old plant grown in an unheated glasshouse with light overhead shade.

DESCRIPTION OF THE NEW VARIETY

The following detailed descriptions set forth the distinctive characteristics of 'Hillyssun'. Observations were collected between Fall 2019 and March 2020 in Oxnard, Calif. from a plant which was growing outdoors in full sun in a 1-gallon container. The plant had been grown naturally and allowed to trail without any pinching or use of chemical growth regulator. Color determinations were made in accordance with The 2007 Royal Horticultural Society Colour Chart from London England, except where general color terms of ordinary dictionary significance are used.

Classification:

*Family*.—Primulaceae.

*Genus.—Lysimachia.*

*Species.—christinae.*

*Common name*.—None known to the inventor.

Parentage: Seedling raised from the species *Lysimachia christinae* (unnamed, unpatented).

Plant:

*Propagation method*.—Stem cuttings retaining at least one node.

*Rooting system*.—Fine and fibrous.

*Vigor*.—Vigorous trailing habit, either prostrate or hanging.

*Time to develop roots*.—4 to 5 weeks are required for a newly planted cutting to become established on its own roots.

*Crop time* (*hanging basket*).—Approximately 4 months are required to produce a flowering plant in a 1 gallon container from a rooted cutting.

*Suggested container size*.—1 gallon container and larger if desired.

*Use*.—Ornamental for use as a hanging basket or container plant.

*Type*.—Perennial in USDA Zone 7 and warmer.

*Overall dimensions*.—After 4 months growth in a 1 gallon, 1 meter in trailing length and 50 cm in diameter at the shoulder.

*Cultural requirements*.—Grow in part shade with moderate water and well-draining soil.

*Hardiness*.—USDA Zone 7.

*Growth habit*.—Prostrate in nature, Hanging and trailing in recommended cultivation.

*Blooming season*.—Summer until fall unless summer flowering dormancy is triggered by prevailing temperatures exceeding 25 degrees Celsius.

*Lastingness of inflorescence*.—Approximately 7 days.

Stems:

*Length*.—1 m at four months.

*Diameter*.—3 mm.

*Color*.—Ranges between RHS 53B and RHS 58A.

*Shape*.—Cylindrical.

*Texture*.—Glabrous.

*Strength*.—Strong and stiff with pronounced apical dominance.

*Lateral stems*.—Rarely present. Where present, lateral stems bear only one or two pairs of leaves.

Leaves:

*Type, arrangement*.—Simple, opposite in pairs at each node.

*Attachment*.—Petiolate.

*Quantity per stem*.—20 to 25 pairs borne on 1 m stems.

*Shape*.—Rounded to rounded-deltoid.

*Dimensions* (*leaf rounded*).—Diameter 3.0 cm to 3.5 cm.

*Dimensions* (*leaf rounded-deltoid*).—Length 3.0 cm to 3.5 cm, width 2.5 cm to 3.0 cm.

*Texture, thickness*.—Leathery, 0.5 mm.

*Leaf color, young and mature leaves, adaxial surface*.—Ranges between 139B and 141B.

*Leaf color, young and mature leaves, abaxial surface*.—138C.

*Venation*.—Pinnate.

*Vein color, young foliage, adaxial surface*.—Same as leaf color, except central vein is N186C.

*Vein color, mature foliage, adaxial surface*.—Same as leaf, except central vein and lateral veins are N186C.

*Vein color, young and mature foliage, abaxial surface*.—138D.

*Surface* (*both surfaces*).—Glaucous.

*Margin*.—Entire.

*Apex*.—Rounded.

*Base*.—Cordate.

Petiole:

*Shape*.—Round.

*Length*.—0.5 cm to 1.5 cm.

*Diameter*.—2 mm.

*Texture*.—Glabrous.

*Color*.—Ranges between RHS 53B and RHS 58A.

Inflorescence:

*Type*.—Campanulate.

*Arrangement*.—Solitary in leaf axil. 1 inflorescence per leaf axil, 2 inflorescences per node.

*Dimensions* (*fully open*).—2.5 cm in diameter, 1.5 cm in depth (petal apex to corolla tube base).

*Number of flowers per stem*.—10 to 12 buds and flowers at any one time.

*Bloom period*.—May to July.

*Lastingness of inflorescence once fully opened*.—7 days.

Pedicel:

*Shape*.—Round.

*Length*.—0.5 cm (bud) to 1.5 cm (flower fully open).

*Diameter*.—3 mm.

*Texture*.—Glabrous.

*Color*.—Ranges between RHS 53B and RHS 58A.

Buds:

*Length* (*before opening*).—0.75 cm.

*Diameter* (*before opening*).—0.5 cm.

*Shape*.—Conical.

*Color*.—RHS 9A, suffused RHS N30A to RHS N30B towards base.

Calyx:

*Shape*.—Campanulate.

*Sepal quantity*.—5, mostly free, fused towards and at base.

*Sepal shape*.—Elliptic-lanceolate; apex acute; base truncate.

*Sepal dimensions*.—5 mm in length, 3 mm in width.

*Sepal color* (*both surfaces*).—RHS 137A where free, RHS 59B towards base.

*Sepal texture* (*both surfaces*).—Lightly pubescent. Smooth, glabrous (both surfaces): Length (before opening): 0.75 cm.

Corolla: Short tube, up to 5 mm in length, before petals diverge.

*Corolla color* (*both surfaces*).—RHS N30A to RHS N30B.

Petals:

*Quantity*.—5, free; fused at base.

*Shape*.—Elliptic.

*Dimensions*.—12 mm to 15 mm in length, 8 mm in width.

*Color* (*both surfaces*).—RHS 9A, suffused RHS N30A to RHS N30B towards base.

*Texture* (*both surfaces*).—Glabrous.

*Apex*.—Rounded, occasionally with small notch 1 mm to 2 mm in width and depth.

*Base*.—Cuneate.

*Margin*.—Smooth, entire except for apical notch where present.

Reproductive organs:

*Stamens*.—5 arranged in close bundle 6 mm to 8 mm in length, 2 mm to 3 mm in diameter, color as petal base, RHS N30A to RHS N30B.

*Anthers*.—Ovate, 1.5 mm in length, 1 mm in width, color (pollen removed) RHS 155B.

*Pollen*.—Present, copious, color 9C.

*Pistil*.—1, 9 mm to 10 mm in length.

*Stigma*.—Capitate, 1.5 mm in diameter, held approximately 1 mm to 2 mm above anthers, color RHS 157D.

*Style*.—6 mm to 8 mm in length, color RHS N30A to RHS N30B.

*Ovary*.—Not observed.

Seed: Not observed.

Disease and pest resistance or susceptibility: None observed.

COMPARISON WITH PARENTAL LINES AND KNOWN VARIETY

'Hillyssun' may be distinguished from plants raised as seedlings from the species parent, *Lysimachia*. In comparison with the species parent, the leaves of 'Hillyssun' exhibit narrow dark-purple veins, especially the central vein or midrib. Most notably, the flowers of 'Hillyssun' are brighter yellow in color with prominent orange-red eyes (petal bases). Flowers of the species are predominantly yellow in color throughout.

'Hillyssun' may be compared to the commercial *Lysimachia christinae* 'Zixin' (unpatented) in that that the veins of 'Hillyssun' are dark-purple in color, while the veins of 'Zixin' appear to be brighter mid-purple in color, and the dark-purple foliage veining of 'Zixin' appears to be significantly broader along the central vein and extends along and adjacent to the lateral veins. The purple veining of 'Hillyssun' in narrow along the central vein and lateral veins and far less conspicuous than 'Zixin'.

I claim:

1. A new and distinct variety of *Lysimachia* plant named 'Hillyssun' as described and illustrated herein.

* * * * *